US012446755B2

(12) United States Patent
Horn et al.

(10) Patent No.: US 12,446,755 B2
(45) Date of Patent: Oct. 21, 2025

(54) SYSTEM AND METHOD FOR DETERMINING PRESENCE OF WATER SOFTENER

(71) Applicant: Haier US Appliance Solutions, Inc., Wilmington, DE (US)

(72) Inventors: Austin Horn, Louisville, KY (US); Noushin Mir, Lousiville, KY (US); Je Kwon Yoon, Hwangseong-si (KR); Seong Hoon Ryu, Suwon-si (KR); Wonmyung Seo, Seongnam-si (KR); Khalid Jamal Mashal, Louisville, KY (US); Oluwatosin Fagbuyi, Louisville, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 375 days.

(21) Appl. No.: 17/971,253

(22) Filed: Oct. 21, 2022

(65) Prior Publication Data

US 2024/0130601 A1 Apr. 25, 2024
US 2024/0225411 A9 Jul. 11, 2024

(51) Int. Cl.
*A47L 15/42* (2006.01)
*A47L 15/00* (2006.01)
(Continued)

(52) U.S. Cl.
CPC ....... *A47L 15/4297* (2013.01); *A47L 15/0028* (2013.01); *A47L 15/0063* (2013.01);
(Continued)

(58) Field of Classification Search
CPC ............. A47L 15/4297; A47L 15/0028; A47L 15/0063; A47L 15/4229; A47L 15/4287;
(Continued)

(56) References Cited

U.S. PATENT DOCUMENTS 8,192,687 B2 6/2012 Chan et al.
8,424,345 B2 4/2013 Park et al.
2011/0253606 A1* 10/2011 Chan ....................... D06F 33/37 210/96.1

FOREIGN PATENT DOCUMENTS

CN 213387988 U 6/2021
DE 102018008118 B4 7/2020
DE 202021101886 U1 4/2021

OTHER PUBLICATIONS

DE202021101886U1—machine translation (Year: 2020).*

* cited by examiner

*Primary Examiner* — Tinsae B Ayalew
(74) *Attorney, Agent, or Firm* — Dority & Manning, P.A.

(57) ABSTRACT

An appliance, system, and method for operating an appliance and determining presence of water softener at water provided to an appliance is provided. The system is configured to obtain a first water hardness value; obtain a second water hardness value based on a location of the appliance; determine a ratio of the first water hardness value and the second water hardness value; compare the ratio of the first water hardness value and the second water hardness value to a threshold limit; transmit a first water hardness signal when the threshold limit is exceeded, wherein the first water hardness signal corresponds to the first water hardness value; transmit, to the database storage device, a second water hardness signal when the ratio is within the threshold limit; and adjust operation of the appliance based on whether the first water hardness signal or the second water hardness signal is transmitted.

20 Claims, 3 Drawing Sheets

(51) Int. Cl.

| | |
|---|---|
| ***A47L 15/44*** | (2006.01) |
| ***A47L 15/46*** | (2006.01) |
| ***D06F 33/36*** | (2020.01) |
| ***D06F 33/37*** | (2020.01) |
| ***D06F 34/04*** | (2020.01) |
| ***D06F 34/22*** | (2020.01) |
| ***D06F 39/00*** | (2020.01) |
| ***G01N 33/18*** | (2006.01) |
| *D06F 103/20* | (2020.01) |

(52) U.S. Cl.
CPC ....... *A47L 15/4229* (2013.01); *A47L 15/4287* (2013.01); *A47L 15/449* (2013.01); *A47L 15/46* (2013.01); *D06F 33/36* (2020.02); *D06F 33/37* (2020.02); *D06F 34/04* (2020.02); *D06F 34/22* (2020.02); *D06F 39/007* (2013.01); *G01N 33/1853* (2013.01); *A47L 2401/11* (2013.01); *A47L 2501/07* (2013.01); *A47L 2501/30* (2013.01); *D06F 2103/20* (2020.02)

(58) Field of Classification Search
CPC .... A47L 15/449; A47L 15/46; A47L 2401/11; A47L 2501/07; A47L 2501/30; D06F 34/22; D06F 33/36; D06F 34/04; D06F 33/37; D06F 39/007; D06F 2103/20; G01N 33/1853
USPC ........................................................ 68/12.01
See application file for complete search history.

SYSTEM AND METHOD FOR DETERMINING PRESENCE OF WATER SOFTENER

FIELD

The present subject matter relates generally to systems and methods for determining the presence of water softener, and more particularly to appliances having systems for determining the presence of water softener and methods for operation.

BACKGROUND

Water conductivity may be impacted if a user is utilizing a water softener at the water supply from which an appliance receives water. Softened water generally has a higher conductivity, which can result in an incorrect water hardness conversion. Incorrect water hardness or changes in water conductivity can adversely affect wash cycles at washing appliances, such as wash duration and ratios of water to detergent, or appliance efficiency.

Accordingly, improved appliances, and systems and methods for operating appliances, that overcome these challenges would be advantageous.

BRIEF DESCRIPTION

Aspects and advantages of the invention will be set forth in part in the following description, or may be understood from the description, or may be learned through practice of the invention.

An aspect of the present disclosure is directed to an appliance. The appliance includes a controller configured to execute operations. The operations include obtaining, at the appliance, a first water hardness value; obtaining a second water hardness value based on a location signal corresponding to a location of the appliance; determining a ratio of the first water hardness value and the second water hardness value; comparing the ratio of the first water hardness value and the second water hardness value to a threshold limit; transmitting, to a database storage device, a first water hardness signal when the threshold limit is exceeded, wherein the first water hardness signal corresponds to the first water hardness value; transmitting, to the database storage device, a second water hardness signal when the ratio is within the threshold limit; and adjusting operation of the appliance based on whether the first water hardness signal or the second water hardness signal is transmitted.

Another aspect of the present disclosure is directed to a system for determining water conductivity. The system includes an appliance configured to receive water from a water supply; a database storage device communicatively coupled to the appliance; and a controller configured to store instructions that, when executed by a processor, causes the appliance and the remote server to perform operations. The operations include obtaining, from the appliance, a first water hardness value corresponding to a first water hardness value; transmitting, from the appliance to the database storage device, a location signal corresponding to a location of the appliance; obtaining, from the database storage device, a second water hardness value based on the location signal; determining a ratio of the first water hardness value and the second water hardness value; comparing the ratio of the first water hardness value and the second water hardness value to a threshold limit; transmitting, to the database storage device, a first water hardness signal when the threshold limit is exceeded, wherein the first water hardness signal corresponds to the first water hardness value; transmitting, to the appliance, a first control signal when the first water hardness signal is transmitted; transmitting, to the database storage device, a second water hardness signal when the ratio is within the threshold limit; and transmitting, to the appliance, a second control signal when the second water hardness signal is transmitted.

Yet another aspect of the present disclosure is directed to a method for operating an appliance based on water softener level in water provided to an appliance. The method includes measuring a first water hardness value at water provided to the appliance; obtaining a second water hardness value based on a geographic location of the appliance; determining a ratio of the first water hardness value and the second water hardness value; comparing the ratio of the first water hardness value and the second water hardness value to a threshold limit; transmitting a first water hardness signal when the threshold limit is exceeded, wherein the first water hardness signal corresponds to the first water hardness value; transmitting a second water hardness signal when the ratio is within the threshold limit; and adjusting operation of the appliance based on whether the first water hardness signal or the second water hardness signal is transmitted, wherein adjusting operation of the appliance includes adjusting one or more of ratio of water to detergent, a water temperature, a wash cycle duration, or a wash cycle agitation.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

Figure 1:
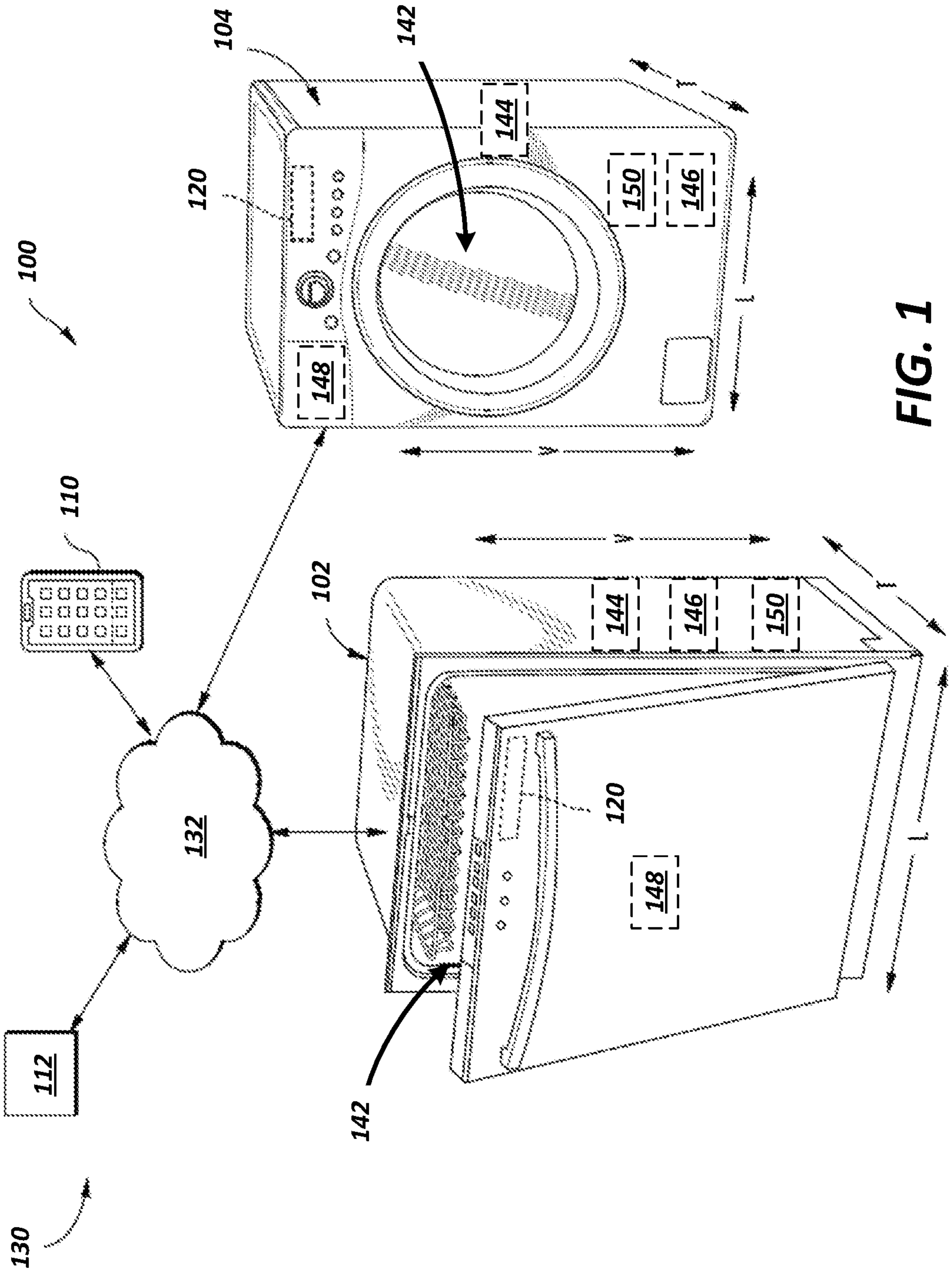
FIG. 1 depicts a schematic embodiment of a computing network for operating an appliance in accordance with aspects of the present disclosure.

Repeat use of reference characters in the present specification and drawings is intended to represent the same or analogous features or elements of the present invention.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first," "second," and "third" may be used interchangeably to distinguish one component from another and are not intended to signify location or importance of the individual components. The terms "includes" and "including" are intended to be inclusive in a manner similar to the term "comprising." Similarly, the term "or" is generally intended to be inclusive (i.e., "A or B" is intended to mean "A or B or both"). In addition, here and throughout the specification and claims, range limitations may be combined or interchanged. Such ranges are identified and include all the sub-ranges contained therein unless context or language indicates otherwise. For example, all ranges disclosed herein are inclusive of the endpoints, and the endpoints are independently combinable with each other. The singular forms "a," "an," and "the" include plural references unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "generally," "about," "approximately," and "substantially," are not to be limited to the precise value specified. In at least some instances, the approximating language may correspond to the precision of an instrument for measuring the value, or the precision of the methods or machines for constructing or manufacturing the components or systems. For example, the approximating language may refer to being within a 10 percent margin (i.e., including values within ten percent greater or less than the stated value). In this regard, for example, when used in the context of an angle or direction, such terms include within ten degrees greater or less than the stated angle or direction (e.g., "generally vertical" includes forming an angle of up to ten degrees in any direction, such as, clockwise or counterclockwise, with the vertical direction V).

Systems and methods for determining the presence of water softener are provided. Aspects of the present disclosure are directed to appliances, such as dishwashing appliances and laundry washing appliances, and methods for operating such appliances based on changes in water conductivity or water hardness. Particular embodiments of the appliance may include variable dispensing devices for detergent, water, or detergent-water mixture, such as to allow for improved wash cycle efficiency. Embodiments of the system and method provided herein measure a water property value (e.g., water conductivity or water hardness) of water provided to the appliance and compare the measured water property value to a database, tabulation, chart, graph, lookup table, or other data source corresponding geographic location to water source and water property value corresponding to the geographic location. Embodiments of the system and method determine a difference between the measured water property value and the database water property value, such as a ratio of measured water property value and database water property value versus a threshold limit. When the difference exceeds the threshold limit, a user may be prompted to indicate whether a water softener is used at the location at which the appliance is placed (e.g., a household). In certain embodiments, operation of the appliance is adjusted based on whether the threshold limit is exceeded or within limit.

Referring now to FIG. 1, a computing network 100 including one or more appliances 102, 104 will be described according to exemplary embodiments of the present subject matter. In general, the network 100 may include any suitable number, type, and configuration of appliances such as described herein, remote servers, network devices, and/or other external devices. Some of these appliances 102, 104 may be able to communicate with each other or are otherwise interconnected. This interconnection, interlinking, and interoperability of multiple appliances and/or devices may commonly be referred to as "smart home" or "connected home" appliance interconnectivity.

FIG. 1 illustrates the computing network 100 according to exemplary embodiments of the present subject matter. As shown, the computing network 100 generally includes one or more appliances 102, 104 configured to circulate, recirculate, drain or otherwise move fluid (e.g., water, wash fluid, detergent, water-detergent mixture, etc.) into, through, and out of a wash chamber. As schematically depicted in FIG. 1, appliance 102, 104 may include a wash chamber 142 at which articles (e.g., dishes, utensils, containers, etc. at appliance 102, or laundry articles, clothing, etc. at appliance 104), such as may be understood in the art. As further understood in the art, appliance 102, 104 includes any appropriate flow device 144 configured to provide, dispense, agitate, eject, spray, distribute, or otherwise move fluid into or through the wash chamber 142. Various embodiments of the flow device 144 may include flow nozzles, valves, rotatable vanes or blades, agitators, or other appropriate flow structures. Various embodiments of appliance 102, 104 may include a pump 146 or other device allowing or promoting flow, or pressurized flow, of fluid into, through, or out of the wash chamber 142. It should be appreciated that "fluid", as provided herein, includes water, water-detergent mixture, detergent, cleaning solution, or combinations thereof, or aerated combinations thereof including a gaseous fluid (e.g., air) mixed therewith.

In certain embodiments, appliance 102, 104 may include a dispensing device 148 configured to hold and selectively dispense a quantity of liquid, solid (e.g., powder), or gel detergent or other cleaning medium. In particular embodiments, dispensing device 148 is configured to hold quantities of cleaning medium appropriate for multiple wash cycles. In still further embodiments, dispensing device 148 is operably coupled to a controller 120 and configured to dispense, or otherwise allow for mixtures with water, various amounts of cleaning medium based on a plurality of operating modes or control signals, such as further described herein.

Appliance 102, 104 includes one or more sensors 150 configured to measure, determine, or otherwise obtain temperature, conductivity, turbidity, or combinations thereof, of water received, cycled through, or operating at appliance 102, 104. Sensor 150 may be configured to obtain temperature, conductivity, or turbidity by any appropriate method or apparatus, including, but not limited to, thermocouples, light sensors, imaging devices (e.g., infrared, ultraviolet, visible light, etc.), or conductivity meters. Sensor 150 may be a single, integral component, or may include a plurality of sensors 150 each configured to generate, obtain, transmit, etc. signals corresponding to temperature, conductivity, or turbidity of water received, cycled through, or operating at appliance 102, 104. Sensor 150 is communicatively and operably coupled to various components of appliance 102, 104, such as controller 120, such as to communicate measurements or measurement signals from sensor 150 to controller 120.

As depicted in FIG. 1, appliance 102 may form a dishwashing appliance and appliance 104 may form a laundry washing appliance. Details regarding the components and operation of appliances 102, 104 may be understood by one having ordinary skill in the art and further detailed discussion is omitted herein for brevity. However, it should be appreciated that the specific appliance types and configurations are only exemplary and are provided to facilitate discussion regarding the use and operation of an exemplary computing network 100 for one or more appliances such as described herein. The scope of the present subject matter is not limited to the specific number, type, and configurations of appliances set forth herein.

In certain embodiments, computing network 100 may include one or more external devices, e.g., devices that are separate from or external to the one or more appliances 102, 104, and which may be configured for facilitating communications with various appliances or other devices. For example, the computing network 100 may include or be communicatively coupled with a remote user interface device 110 that may be configured to allow user interaction with some or all appliances 102, 104 or other devices in the computing network 100.

In general, remote user interface device 110 may be any suitable device separate and apart from appliances 102, 104 that is configured to provide or receive communications, information, data, or commands from a user, such as further described herein. In this regard, remote user interface device 110 may be an additional user interface to the user interface panels of the various appliances within the computing network 100. In this regard, for example, the user interface device 110 may be a personal phone, a smartphone, a tablet, a laptop or personal computer, a wearable device, a smart home system, or another mobile or remote device. For example, the separate device may be a smartphone operable to store and run applications, also known as "apps," and the user interface device 110 be provided as a smartphone app.

In still particular embodiments, user interface device 110 may be affixed to or form a part of another appliance (e.g., refrigeration appliance), such as may provide for centralized communication among a plurality of appliances including one or more of appliances 102, 104. Appliances to which user interface device 110 is operably coupled may be configured substantially similarly as a personal phone, a smartphone, a tablet, a laptop or personal computer, a wearable device, a smart home system, or another mobile or remote device.

As will be described in more detail below, some or all of the computing network 100 may include or be communicatively coupled with a database storage device or remote server 112 that may be in operative communication with some or all appliances within computing network 100. Thus, in certain embodiments, user interface device 110 and/or remote server 112 may refer to one or more devices that are not considered dishwashing or laundry appliances as used herein. In addition, devices such as a personal computer, router, network devices, and other similar devices whose primary functions are network communication and/or data processing are not considered dishwashing or laundry appliances as used herein.

As illustrated, each of appliance 102, 104, user interface device 110, or any other devices or appliances in computing network 100 may include or be operably coupled to a controller 120. Controller 120 is configured to regulate operation at appliance 102, 104. The controller 120 may be positioned in a variety of locations throughout appliance 102, 104 (e.g., a control panel area, at a door, etc.). In some embodiments, input/output ("I/O") signals are routed between controller 120 and various operational components of appliance 102, 104 along wiring harnesses that may be routed, e.g., through the bottom of a door. Controller 120 may include a user interface panel through which a user may select various operational features and operating modes and monitor progress of the appliance 102, 104. The user interface may represent a general purpose I/O ("GPIO") device or functional block. Additionally, the user interface may include input components, such as one or more of a variety of electrical, mechanical, or electro-mechanical input devices including rotary dials, push buttons, and touch pads. The user interface may also include a display component, such as a digital or analog display device designed to provide operational feedback to a user. The user interface may be in communication with the controller 120 via one or more signal lines or shared communication busses.

As used herein, the terms "processing device," "computing device," "controller," or the like may generally refer to any suitable processing device, such as a general or special purpose microprocessor, a microcontroller, an integrated circuit, an application specific integrated circuit (ASIC), a digital signal processor (DSP), a field-programmable gate array (FPGA), a logic device, one or more central processing units (CPUs), a graphics processing units (GPUs), processing units performing other specialized calculations, semiconductor devices, etc. In addition, these "controllers" are not necessarily restricted to a single element but may include any suitable number, type, and configuration of processing devices integrated in any suitable manner to facilitate appliance operation. Alternatively, controller 120 may be constructed without using a microprocessor, e.g., using a combination of discrete analog and/or digital logic circuitry (such as switches, amplifiers, integrators, comparators, flip-flops, AND/OR gates, and the like) to perform control functionality instead of relying upon software.

Controller 120, user interface device 110, and remote server 112 may include, or be associated with, one or more memory elements or non-transitory computer-readable storage mediums, such as RAM, ROM, EEPROM, EPROM, flash memory devices, magnetic disks, or other suitable memory devices (including combinations thereof). These memory devices may be a separate component from the processor or may be included onboard within the processor. In addition, these memory devices can store information and/or data accessible by the one or more processors, including instructions that can be executed by the one or more processors. It should be appreciated that the instructions can be software written in any suitable programming language or can be implemented in hardware. Additionally, or alternatively, the instructions can be executed logically and/or virtually using separate threads on one or more processors. Executed instructions cause the computing network 100, or the appliances 102, 104, remote server 112, or user interface device 110 in particular, to perform operations, such as one or more steps of method 1000 provided further herein.

For example, controller 120 may be operable to execute programming instructions or micro-control code associated with an operating cycle or operating mode of appliance 102, 104. In this regard, the instructions may be software or any set of instructions that when executed by the processing device, cause the processing device to perform operations, such as running one or more software applications, displaying a user interface, receiving user input signals, processing user input signals, adjusting a ratio of water to detergent, adjusting a water temperature, adjusting a wash cycle duration, adjusting a wash cycle agitation, speed, turbidity, or other performance parameter, or other operational parameter associated with a wash cycle speed, intensity, effectiveness, efficiency, detergent use, or detergent-water mixture.

Moreover, it should be noted that controller 120 as disclosed herein is additionally, or alternatively, configured to store, execute, or otherwise operate or perform any one or more methods, method steps, or portions of methods as disclosed herein. For example, in some embodiments, methods disclosed herein may be embodied in programming instructions stored in the memory at one or more of controller 120, user interface device 110, or remote server 112, and executed by controller 120, user interface device 110, or remote server 112. The memory devices may also store data that can be retrieved, manipulated, created, or stored by the one or more processors or portions of controller 120. One or more database(s) can be connected to controller 120 through any suitable communication module, communication lines, or network(s) (e.g., computing network 1320. Such databases, as further described herein, are stored at one or more of controller 120, user interface device 110, remote server 112.

Referring still to FIG. 1, a schematic diagram of an external communication system 130 will be described according to an exemplary embodiment of the present subject matter. In general, external communication system 130 is configured for permitting interaction, data transfer, and other communications between and among one or more of the appliances 102, 104 user interface device 110, and the remote server 112. For example, this communication may be used to transmit packets of data or datasets through a network 132 and to the remote server 112 and to receive at one or more appliances 102, 104 one or more control signals, user signals, location signals, water property signals (e.g., water hardness, water conductivity, etc.) or other signals or adjustments corresponding to one or more of operating parameters, cycle settings, user instructions or notifications, performance characteristics, user preferences, or any other suitable information for improved performance of one or more appliances within system of appliances 100.

In addition, remote server 112 may be in communication with the appliance 102, 104 and/or user interface device 110 through the network 132. In this regard, for example, remote server 112 may be a cloud-based server 112, and is thus located at a distant location, such as in a separate state, country, etc. According to an exemplary embodiment, user interface device 110 may communicate with a remote server 112 over network 132, such as the Internet, to transmit/receive signals, data packets or information, datasets, provide user inputs, receive user notifications or instructions, access databases, interact with or control the appliance 102, 104, etc. In addition, user interface device 110 and server 112 may communicate with the appliance 102, 104 to communicate similar information.

In general, communication between the appliance 102, 104, user interface device 110, server 112, and/or other user devices or appliances may be carried using any type of wired or wireless connection and using any suitable type of communication network, non-limiting examples of which are provided below. For example, user interface device 110 may be in direct or indirect communication with the appliance 102, 104 through any suitable wired or wireless communication connections or interfaces, such as network 132. For example, network 132 may include one or more of a local area network (LAN), a wide area network (WAN), a personal area network (PAN), the Internet, a cellular network, any other suitable short- or long-range wireless networks, etc. In addition, communications may be transmitted using any suitable communications devices or protocols, such as via Wi-Fi®, Bluetooth®, Zigbee®, wireless radio, laser, infrared, Ethernet type devices and interfaces, etc. In addition, such communication may use a variety of communication protocols (e.g., TCP/IP, HTTP, SMTP, FTP), encodings or formats (e.g., HTML, XML), and/or protection schemes (e.g., VPN, secure HTTP, SSL).

Communication system 130 is described herein according to an exemplary embodiment of the present subject matter. However, it should be appreciated that the exemplary functions and configurations of communication system 130 provided herein are used only as examples to facilitate description of aspects of the present subject matter. System configurations may vary, other communication devices may be used to communicate directly or indirectly with one or more associated appliances, other communication protocols and steps may be implemented, etc. These variations and modifications are contemplated as within the scope of the present subject matter.

Figure 2:
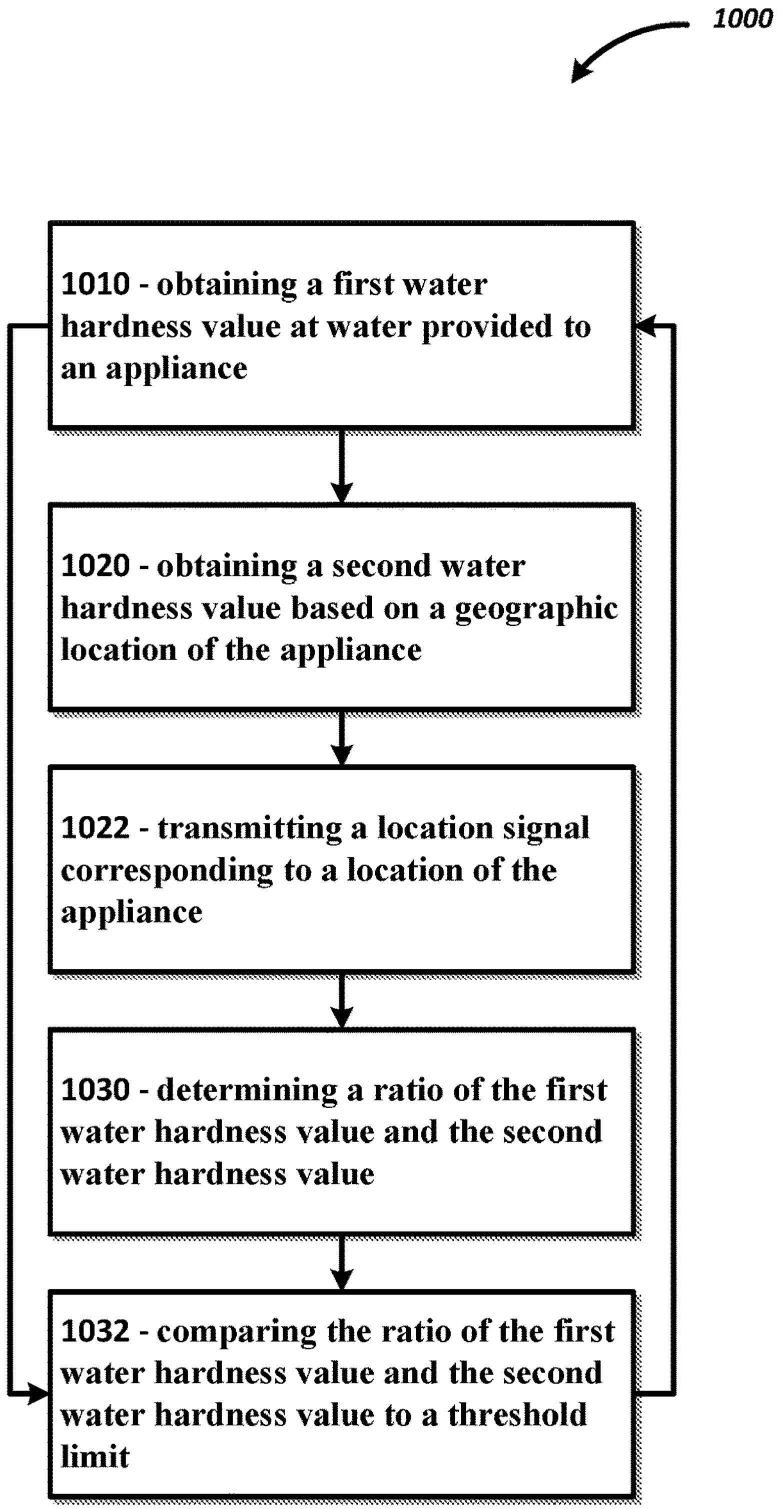
FIG. 2 provides a flowchart outlining steps of an exemplary embodiment of a method for operating an appliance in accordance with aspects of the present disclosure.
Figure 3:
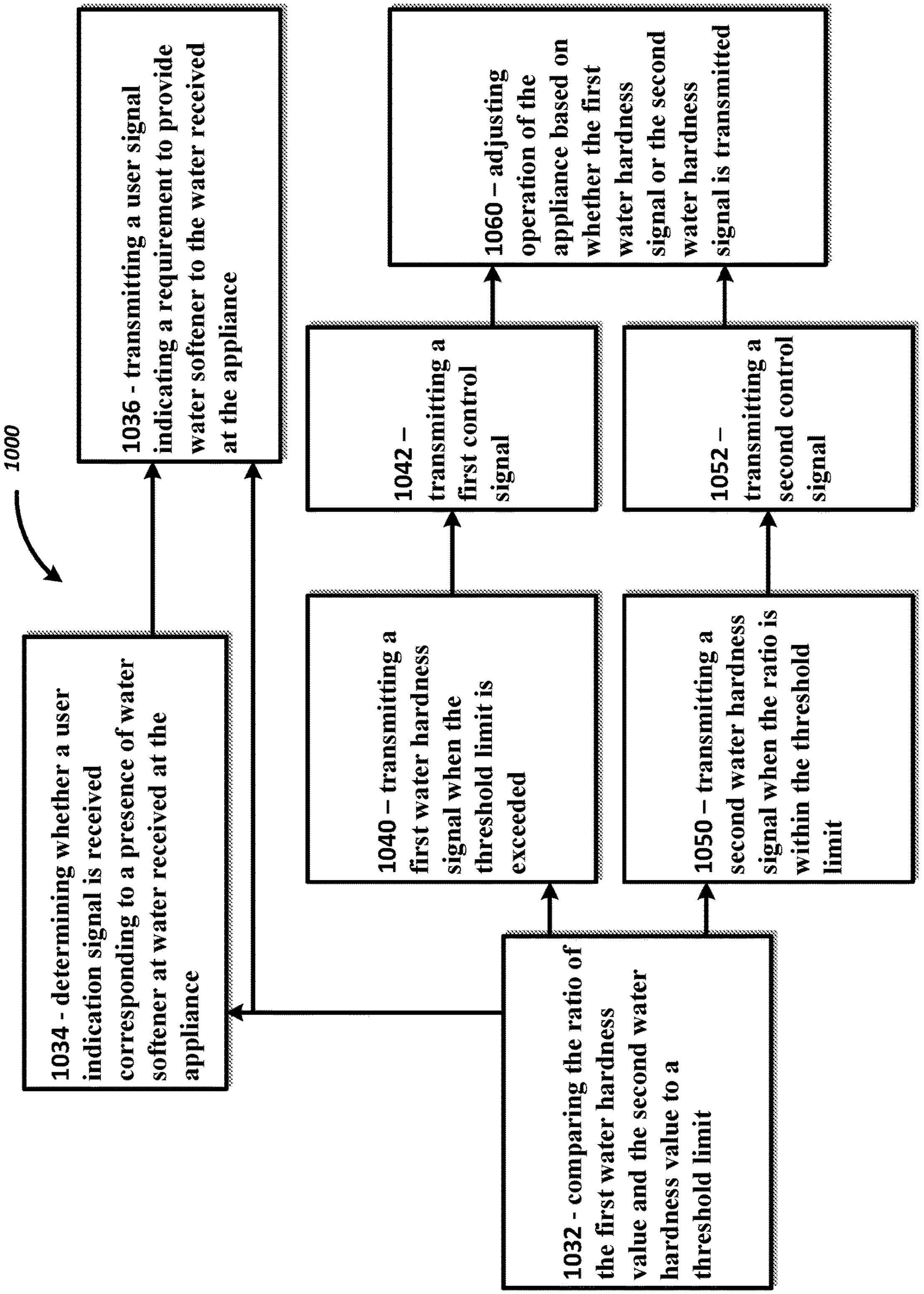
FIG. 3 provides a flowchart outlining steps of an exemplary embodiment of a method for operating an appliance in accordance with aspects of the present disclosure.

Referring now to FIG. 2, a flowchart outlining exemplary steps of a method for operating an appliance (e.g., appliance 102, 104) is provided (hereinafter, "method 1000"). In particular embodiments, method 1000 provides steps for operating a dishwashing appliance or laundry washing appliance. Embodiments of the method 1000, when stored or executed at one or more of controller 120, server 112, or user interface device 110, or generally stored, accessed, or executed across computing network 100, form a system for determining a water property (e.g., water conductivity, water hardness, etc.) and operating the appliance 102, 104 based on the water property.

Method 1000 includes at 1010 measuring, calculating, determining, or otherwise obtaining a first water property value at water provided to an appliance (e.g., appliance 102, 104). In particular embodiments, the first water property value includes a first water hardness value obtained from a sensor (e.g., sensor 150 at appliance 102, 104). The first water property value may include a first water conductivity value, such as from a sensor forming a conductivity meter. Still various embodiments may include obtaining a temperature of water provided to or received at the appliance, or obtaining a turbidity of water at the appliance. Certain embodiments of method 1000 include determining or calculating a first water hardness value from a measured conductivity value obtained by the sensor, or additionally, from a measured temperature value, a measured turbidity value, or both. In certain embodiments, the system may determine the first water property value via transmitting the measured water property value via network 132 from controller 120 to user interface 110 or server 112.

Method 1000 includes at 1020 obtaining a second water hardness value based on a geographic location of the appliance. In particular embodiments, obtaining the second water hardness value includes determining, based at least on a location signal, the second water hardness value from a water supply from which the appliance receives water. In certain embodiments, method 1000 includes at 1022 transmitting to a database storage device (e.g., server 112, user interface device 110) a location signal corresponding to a location, such as the geographic location, of the appliance. In particular embodiments, the appliance (e.g., appliance 102, 104) transmits the location signal corresponding to the geographic location of the appliance. In still various embodiments, a user, such as via user interface device 112, transmits the location signal corresponding to the geographic location of the appliance.

The second water hardness value corresponds to geographic water hardness datasets, tables, graphs, charts, etc., such as corresponding to local or municipal water supplies or reservoirs, underground or well water, captured rainwater, water provided to the location (e.g., water provided via a tanker or other supply vehicle), or other water supplies. The second water hardness value is obtained and stored at any one or more locations at the network 100, such as the controller 120, the server 112, the user interface device 110, or generally accessed from the cloud computing network 132.

In various embodiments, method 1000 includes at 1030 determining a ratio of the first water hardness value and the second water hardness value. The second water hardness value corresponding to geographic water hardness data for water received at the appliance is compared to the first water hardness value corresponding to the measured or calculated water hardness at the appliance (e.g., measured or calculated via sensor 150). Method 1000 includes at 1032 comparing the ratio of the first water hardness value and the second water hardness value to a threshold limit. The threshold limit includes any one or more predetermined values, magnitudes, or limits corresponding to a substantial difference in measured water hardness at the appliance versus expected water hardness corresponding to the water supply. Substantial differences between the first water hardness value and the second water hardness value may be indicative of the presence of a water softener at the water received at the appliance. Water conductivity measurements or calculations may be substantially altered due to the presence of water softener in the water, which may subsequently affect detergent dispensing systems (e.g., dispensing device 148) and ratios of water to detergent, water temperature, wash cycle duration, wash cycle agitation, or other operating parameters at the appliance. For instance, the presence of water softener may lead to higher water conductivity and may require adjusting water hardness conversion and operating parameters at the appliance, such as to maintain or improve efficiency, wash performance, or reduce waste.

In certain embodiments, method 1000 includes at 1034 determining whether a user indication signal is received, in which the user indication signal corresponds to a presence of water softener at water received at the appliance. In a particular embodiment, method 1000 at 1034 occurs when the threshold limit is exceeded. The user indication signal may particularly correspond to a prompt inquiring whether the user uses or has added a water softener to the water provided to the appliance.

In still particular embodiments, method 1000 includes at 1036 transmitting a user signal indicating a requirement to provide water softener to the water received at the appliance. The user signal may be a visual, audible, or other sensory signal emitted from the appliance 102, 104 or the user interface device 110. In certain embodiments, transmitting the user signal occurs after an iteration of step 1010 and step 1032. In such embodiments, transmitting the user signal occurs after one or more iterations of obtaining the first water hardness value and comparing the first water hardness value and the second water hardness value. In still particular embodiments, method 1000 may include transmitting the user signal after one or more iterations at step 1010 and step 1032. Method 1000 may include one or more iterations in which the difference between the first water hardness and the second water hardness is within the threshold limit (i.e., insubstantial differences between measured water hardness and expected water hardness). After one or more such iterations, method 1000 may determine the difference has exceeded the threshold limit and indicative of a requirement to provide water softener to the water provided to the appliance.

In various embodiments, method 1000 includes at 1040 transmitting a first water hardness signal when the threshold limit is exceeded. In certain embodiments, method 1000 at 1040 includes transmitting, to a database storage device, the first water hardness signal when the threshold limit is exceeded. The first water hardness signal corresponds to the first water hardness value, or particularly, the water hardness value measured at the appliance.

In still various embodiments, method 1000 includes at 1050 transmitting a second water hardness signal when the ratio is within the threshold limit. In certain embodiments, method 1000 at 1050 includes transmitting, to the database storage device, the second water hardness signal when the threshold limit is exceeded. The second water hardness signal corresponds to the second water hardness value, or particularly, the water hardness value corresponding to the geographic water hardness data for water received at the appliance.

Method 1000 includes at 1060 altering, changing, modifying, or otherwise adjusting operation of the appliance based on whether the first water hardness signal or the second water hardness signal is transmitted. Adjusting operation of the appliance includes modifying a ratio of water to detergent, water temperature, wash cycle duration, wash cycle agitation, or other operating parameters at the appliance.

In various embodiments, method 1000 includes at 1042 transmitting a first control signal when the first water hardness signal is transmitted. In certain embodiments, method 1000 at 1042 includes transmitting, to the appliance, the first control signal when the first water hardness signal is transmitted at 1040. In still various embodiments, method 1000 includes at 1052 transmitting a second control signal when the second water hardness signal is transmitted. In certain embodiments, method 1000 at 1052 includes transmitting, to the appliance, the second control signal when the second water hardness signal is transmitted at 1050. The first control signal and the second control signal each correspond to an adjustment at the appliance of an operating parameter at the appliance. In various embodiments, the first and second control signals each correspond to changes or modifications in operation of a detergent dispensing system (e.g., dispensing device 148), a water inlet valve (e.g., flow control device 144), or pump (e.g., pump 146), or agitator, such as to alter, change, or modify a ratio of water to detergent, water temperature, wash cycle duration, wash cycle agitation, or other operating parameters at the appliance. For instance, the presence of water softener may lead to higher water conductivity and may require adjusting water hardness conversion and operating parameters at the appliance to maintain or improve efficiency, wash performance, or reduce waste.

Systems and methods for determining the presence of water softener and operating a washing appliance are provided herein based on changes in water conductivity or water hardness. Particular embodiments of the appliance may include modifying detergent or water mixtures from variable dispensing devices for detergent, water, or detergent-water mixture, such as to allow for improved wash cycle efficiency. Embodiments of the system and method provided herein measure a water property value (e.g., first water hardness or water conductivity) of water provided to the appliance and compare the measured water property value to a database, tabulation, chart, graph, lookup table, or other data source corresponding geographic location to water source and water property value corresponding to the geographic location (e.g., second water hardness or water conductivity). Operation of the appliance is adjusted based on whether a threshold limit of difference between first and second water property values is exceeded or within limit, such as to allow for changes in ratio of water to detergent, water temperature, wash cycle duration, wash cycle agitation, or other operating parameters at the appliance.

It should be appreciated that the present subject matter is not limited to any particular style, model, or configuration of dishwashing or laundry washing appliance. Exemplary embodiments depicted and described herein are provided for illustrative purposes only.

Further aspects of the present disclosure are provided in one or more of the following clauses:

1. An appliance, the appliance including a controller configured to execute operations, the operations including obtaining, at the appliance, a first water hardness value; obtaining a second water hardness value based on a location signal corresponding to a location of the appliance; determining a ratio of the first water hardness value and the second water hardness value; comparing the ratio of the first water hardness value and the second water hardness value to a threshold limit; transmitting, to a database storage device, a first water hardness signal when the threshold limit is exceeded, wherein the first water hardness signal corresponds to the first water hardness value; transmitting, to the database storage device, a second water hardness signal when the ratio is within the threshold limit; and adjusting operation of the appliance based on whether the first water hardness signal or the second water hardness signal is transmitted.

2. The appliance of any one or more clauses herein, wherein obtaining the first water hardness value includes measuring the first water hardness value.

3. The appliance of any one or more clauses herein, wherein obtaining the second water hardness value includes determining, based at least on the location signal, the second water hardness value from a water supply from which the appliance receives water.

4. The appliance of any one or more clauses herein, the operations including when the threshold limit is exceeded, determining whether a user indication signal is received, the user indication signal corresponding to a presence of water softener at water received at the appliance.

5. The appliance of any one or more clauses herein, the operations including transmitting a user signal indicating a requirement to provide water softener to the water received at the appliance.

6. The appliance of any one or more clauses herein, wherein transmitting the user signal occurs after an iteration of obtaining the first water hardness value and comparing the first water hardness value and the second water hardness value.

7. The appliance of any one or more clauses herein, wherein adjusting operation of the appliance includes adjusting one or more of a ratio of water to detergent, a water temperature, a wash cycle duration, or a wash cycle agitation.

8. The appliance of any one or more clauses herein, wherein the appliance is a dishwashing appliance.

9. The appliance of any one or more clauses herein, wherein the appliance is a laundry washing appliance.

10. A system for determining water conductivity, the system including an appliance configured to receive water from a water supply; a database storage device communicatively coupled to the appliance; and a controller configured to store instructions that, when executed by a processor, causes the appliance and the remote server to perform operations, the operations including obtaining, from the appliance, a first water hardness value corresponding to a first water hardness value; transmitting, from the appliance to the database storage device, a location signal corresponding to a location of the appliance; obtaining, from the database storage device, a second water hardness value based on the location signal; determining a ratio of the first water hardness value and the second water hardness value; comparing the ratio of the first water hardness value and the second water hardness value to a threshold limit; transmitting, to the database storage device, a first water hardness signal when the threshold limit is exceeded, wherein the first water hardness signal corresponds to the first water hardness value; transmitting, to the appliance, a first control signal when the first water hardness signal is transmitted; transmitting, to the database storage device, a second water hardness signal when the ratio is within the threshold limit; and transmitting, to the appliance, a second control signal when the second water hardness signal is transmitted.

11. The system of any one or more clauses herein, wherein obtaining the second water hardness value includes determining, based at least on the location signal, the second water hardness value from a water supply from which the appliance receives water.

12. The system of any one or more clauses herein, the operations including when the threshold limit is exceeded, determining whether a user indication signal is received, the user indication signal corresponding to a presence of water softener at water received at the appliance.

13. The system of any one or more clauses herein, the operations including transmitting a user signal indicating a requirement to provide water softener to the water received at the appliance.

14. The system of any one or more clauses herein, wherein transmitting the user signal occurs after an iteration of obtaining the first water hardness value and comparing the first water hardness value and the second water hardness value.

15. The system of any one or more clauses herein, wherein the first control signal and the second control signal each correspond to an adjustment at the appliance of one or more of a ratio of water to detergent, a water temperature, a wash cycle duration, or a wash cycle agitation.

16. The system of any one or more clauses herein, wherein the appliance is a dishwashing appliance.

17. The system of any one or more clauses herein, wherein the appliance is a laundry washing appliance.

18. A method for operating an appliance based on water softener level in water provided to an appliance, the method including measuring a first water hardness value at water provided to the appliance; obtaining a second water hardness value based on a geographic location of the appliance; determining a ratio of the first water hardness value and the second water hardness value; comparing the ratio of the first water hardness value and the second water hardness value to a threshold limit; transmitting a first water hardness signal when the threshold limit is exceeded, wherein the first water hardness signal corresponds to the first water hardness value; transmitting a second water hardness signal when the ratio is within the threshold limit; and adjusting operation of the appliance based on whether the first water hardness signal or the second water hardness signal is transmitted, wherein adjusting operation of the appliance includes adjusting one or more of ratio of water to detergent, a water temperature, a wash cycle duration, or a wash cycle agitation.

19. The method of any one or more clauses herein, the method including when the threshold limit is exceeded, determining whether a user indication signal is received, the user indication signal corresponding to a presence of water softener at water received at the appliance.

20. The method of any one or more clauses herein, the method including transmitting a user signal indicating a requirement to provide water softener to the water received at the appliance, wherein transmitting the user signal occurs after an iteration of obtaining the first water hardness value and comparing the first water hardness value and the second water hardness value.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An appliance, the appliance comprising a controller configured to execute operations, the operations comprising:

obtaining, at the appliance, a first water hardness value;

obtaining a second water hardness value based on a location signal corresponding to a location of the appliance;

determining a ratio of the first water hardness value and the second water hardness value;

comparing the ratio of the first water hardness value and the second water hardness value to a threshold limit;

transmitting, to a database storage device, a first water hardness signal when the threshold limit is exceeded, wherein the first water hardness signal corresponds to the first water hardness value;

transmitting, to the database storage device, a second water hardness signal when the ratio is within the threshold limit; and adjusting operation of the appliance based on whether the first water hardness signal or the second water hardness signal is transmitted.

2. The appliance of claim 1, wherein obtaining the first water hardness value comprises measuring the first water hardness value.

3. The appliance of claim 2, wherein obtaining the second water hardness value comprises determining, based at least on the location signal, the second water hardness value from a water supply from which the appliance receives water.

4. The appliance of claim 1, the operations comprising:

when the threshold limit is exceeded, determining whether a user indication signal is received, the user indication signal corresponding to a presence of water softener at water received at the appliance.

5. The appliance of claim 4, the operations comprising:

transmitting a user signal indicating a requirement to provide water softener to the water received at the appliance.

6. The appliance of claim 5, wherein transmitting the user signal occurs after an iteration of obtaining the first water hardness value and comparing the first water hardness value and the second water hardness value.

7. The appliance of claim 1, wherein adjusting operation of the appliance comprises adjusting one or more of a ratio of water to detergent, a water temperature, a wash cycle duration, or a wash cycle agitation.

8. The appliance of claim 1, wherein the appliance is a dishwashing appliance.

9. The appliance of claim 1, wherein the appliance is a laundry washing appliance.

10. A system for determining water conductivity, the system comprising:

an appliance configured to receive water from a water supply;

a database storage device communicatively coupled to the appliance; and a controller configured to store instructions that, when executed by a processor, causes the appliance and a remote server to perform operations, the operations comprising:

obtaining, from the appliance, a first water hardness value;

transmitting, from the appliance to the database storage device, a location signal corresponding to a location of the appliance;

obtaining, from the database storage device, a second water hardness value based on the location signal;

determining a ratio of the first water hardness value and the second water hardness value;

comparing the ratio of the first water hardness value and the second water hardness value to a threshold limit;

transmitting, to the database storage device, a first water hardness signal when the threshold limit is exceeded, wherein the first water hardness signal corresponds to the first water hardness value;

transmitting, to the appliance, a first control signal when the first water hardness signal is transmitted;

transmitting, to the database storage device, a second water hardness signal when the ratio is within the threshold limit; and transmitting, to the appliance, a second control signal when the second water hardness signal is transmitted.

11. The system of claim 10, wherein obtaining the second water hardness value comprises determining, based at least on the location signal, the second water hardness value from a water supply from which the appliance receives water.

12. The system of claim 10, the operations comprising:

when the threshold limit is exceeded, determining whether a user indication signal is received, the user indication signal corresponding to a presence of water softener at water received at the appliance.

13. The system of claim 12, the operations comprising:

transmitting a user signal indicating a requirement to provide water softener to the water received at the appliance.

14. The system of claim 13, wherein transmitting the user signal occurs after an iteration of obtaining the first water hardness value and comparing the first water hardness value and the second water hardness value.

15. The system of claim 10, wherein the first control signal and the second control signal each correspond to an adjustment at the appliance of one or more of a ratio of water to detergent, a water temperature, a wash cycle duration, or a wash cycle agitation.

16. The system of claim 10, wherein the appliance is a dishwashing appliance.

17. The system of claim 10, wherein the appliance is a laundry washing appliance.

18. A method for operating a laundry appliance based on a water conductivity of water provided to the laundry appliance, the method comprising:

measuring a first water hardness value at water provided to the appliance;

obtaining a second water hardness value based on a geographic location of the laundry appliance;

determining a ratio of the first water hardness value and the second water hardness value;

comparing the ratio of the first water hardness value and the second water hardness value to a threshold limit;

transmitting a first water hardness signal when the threshold limit is exceeded, wherein the first water hardness signal corresponds to the first water hardness value;

transmitting a second water hardness signal when the ratio is within the threshold limit; and adjusting operation of the laundry appliance based on whether the first water hardness signal or the second water hardness signal is transmitted, wherein adjusting operation of the laundry appliance comprises adjusting one or more of ratio of water to detergent, a water temperature, a wash cycle duration, or a wash cycle agitation.

19. The method of claim 18, the method comprising:

when the threshold limit is exceeded, determining whether a user indication signal is received, the user indication signal corresponding to a presence of water softener at water received at the laundry appliance.

20. The method of claim 18, the method comprising:

transmitting a user signal indicating a requirement to provide water softener to the water received at the laundry appliance, wherein transmitting the user signal occurs after an iteration of obtaining the first water hardness value and comparing the first water hardness value and the second water hardness value.

* * * * *